(12) United States Patent
Anderson et al.

(10) Patent No.: US 7,659,301 B2
(45) Date of Patent: Feb. 9, 2010

(54) METHODS AND DEVICES FOR EPITHELIAL PROTECTION DURING PHOTODYNAMIC THERAPY

(75) Inventors: Richard Rox Anderson, Lexington, MA (US); Bernhard Ortel, Boston, MA (US); Edwin K. Joe, New York, NY (US)

(73) Assignee: The General Hospital Corporation, Boston, MA (US)

( * ) Notice: Subject to any disclaimer, the term of this patent is extended or adjusted under 35 U.S.C. 154(b) by 718 days.

(21) Appl. No.: 10/709,122

(22) Filed: Apr. 14, 2004

(65) Prior Publication Data

US 2004/0259855 A1    Dec. 23, 2004

Related U.S. Application Data

(60) Provisional application No. 60/462,937, filed on Apr. 15, 2003.

(51) Int. Cl.
| | |
|---|---|
| *A61B 8/00* | (2006.01) |
| *A01N 43/38* | (2006.01) |
| *A01N 37/12* | (2006.01) |
| *A01N 37/44* | (2006.01) |
| *A61K 31/195* | (2006.01) |
| *C07B 47/00* | (2006.01) |
| *C07D 487/22* | (2006.01) |
| *C07C 229/00* | (2006.01) |
| *A61N 5/02* | (2006.01) |
| *A61N 1/39* | (2006.01) |

(52) U.S. Cl. .................. 514/410; 514/561; 514/859; 514/863; 540/145; 562/567; 424/9.61; 600/2; 607/1

(58) Field of Classification Search ............. 514/410, 514/561, 859, 863; 540/145; 562/567; 424/9.61; 600/2; 607/1
See application file for complete search history.

(56) References Cited

U.S. PATENT DOCUMENTS

| | | | | |
|---|---|---|---|---|
| 5,114,973 | A | * | 5/1992 | Hess et al. .................. 514/557 |
| 5,451,576 | A | | 9/1995 | Sessler et al. |
| 5,643,334 | A | | 7/1997 | Eckhouse et al. |
| 5,709,654 | A | * | 1/1998 | Klatz et al. .................. 604/24 |
| 5,763,235 | A | * | 6/1998 | Watanabe et al. ........... 435/128 |
| 5,784,162 | A | | 7/1998 | Cabib et al. |
| 5,955,490 | A | * | 9/1999 | Kennedy et al. ............. 514/410 |
| 6,050,990 | A | * | 4/2000 | Tankovich et al. ............. 606/9 |
| 6,099,521 | A | | 8/2000 | Shadduck |
| 6,162,242 | A | | 12/2000 | Peyman |
| 6,180,402 | B1 | | 1/2001 | Granville et al. |
| 6,358,242 | B1 | | 3/2002 | Cecchetti |
| 6,365,145 | B1 | | 4/2002 | Ben-Hur et al. |
| 6,443,976 | B1 | | 9/2002 | Flower et al. |
| 2002/0127230 | A1 | | 9/2002 | Chen |

FOREIGN PATENT DOCUMENTS

JP    10-165410    6/1998

OTHER PUBLICATIONS

Fritsch, C. et al., "Photodynamic Therapy in Dermatology," Arch. Dermatol. 134:207-14 (1998).

* cited by examiner

*Primary Examiner*—Johann R Richter
*Assistant Examiner*—Luke E Karpinski
(74) *Attorney, Agent, or Firm*—Nutter McClennen & Fish LLP

(57) ABSTRACT

Methods for preventing damage to the epidermis during PDT induced using a pre-photosensitizing agent are provided. The methods of the present invention utilize spatial confinement to control formation of a photoactive species from a topically-applied pre-photosensitizing agent. In one embodiment, thermal inhibition is used to prevent the metabolism of a pre-photosensitizing agent in epithelial tissue surrounding a treatment site. In another embodiment, a chemical inhibitor can be applied to the epithelial tissue to inhibit the conversion of a pre-photosensitizing agent into a phototoxic species.

25 Claims, 7 Drawing Sheets

METHODS AND DEVICES FOR EPITHELIAL PROTECTION DURING PHOTODYNAMIC THERAPY

CROSS REFERENCE TO RELATED APPLICATIONS

This application claims priority from U.S. Provisional Patent Application Ser. No. 60/462,937, filed on Apr. 15, 2003, entitled "Methods for Epidermal Protection During Photodynamic Therapy," which is expressly incorporated by reference herein.

FIELD OF THE INVENTION

The present invention relates to methods for protecting epithelial tissue during photodynamic therapy using thermal and/or chemical inhibition.

BACKGROUND OF THE INVENTION

Photodynamic therapy (PDT), which can be used for many purposes including hair removal and acne treatment, involves the combination of a light-absorbing photosensitizing agent with light of the appropriate wavelength. A pre-photosensitizer, such as aminolevulinic acid (ALA, ALA-ester), which converts into a photosensitizing agent when it metabolizes, can also be used. The photosensitizing agent or pre-photosensitizing agent is topically or systemically applied to a target tissue where it accumulates. Upon irradiation with a visible light of an activating wavelength, the photosensitizing agent causes the release of reactive oxygen species in cells containing the photosensitizing agent, thereby promoting cell death.

While PDT induced using a photosensitizing agent or pre-photosensitizing agent has been somewhat successful, it can be difficult to control the treatment area. In particular, the photosensitizing agent or pre-photosensitizing agent can accumulate in healthy tissues as well as the target tissue. In hair removal, for example, the photosensitizing agent or pre-photosensitizing agent is applied to the skin topically and is absorbed by both the epidermal and dermal layers of the skin. As a result, application of light can cause phototoxicity to the epidermis, which can lead to long-lasting hyperpigmentation or epidermal necrosis.

Accordingly, there is a need for improved methods for photodynamic therapy that reduce or eliminate damage to epithelial tissue while allowing treatment of underlying targeted tissue.

BRIEF SUMMARY OF THE INVENTION

The present invention generally provides methods for controlling the application of PDT induced using a pre-photosensitizing agent, and in particular for preventing damage to epithelial tissue, such as the epidermis, during PDT. In general, the method includes the step of administering a pre-photosensitizing agent, such as a porphyrin precursor, to a targeted treatment site. This can be achieved, for example, by topically applying the pre-photosensitizing agent to epithelial tissue surrounding the targeted treatment site. The pre-photosensitizing agent is then absorbed through the tissue and into tissue at the targeted treatment site, where it metabolizes to convert into a photosensitizing agent, such as a porphyin. The method further includes the steps of preventing metabolism of the photosensitizing agent in epithelial tissue surrounding the targeted treatment site, and irradiating the treatment site to activate the photosensitizing agent, e.g., to cause phototoxicity, at the targeted treatment site such that the epithelial tissue surrounding the targeted treatment site is substantially unaffected.

In one embodiment, metabolism of the pre-photosensitizing agent in non-targeted epithelial tissue surrounding the targeted treatment site can be prevented by thermal inhibition, and in particular by creating a temperature gradient between the non-targeted epithelial tissue and tissue at the targeted treatment site. The temperature gradient can be created by cooling the non-targeted epithelial tissue and/or by heating the tissue at the targeted treatment site underlying the epithelial tissue.

The present invention also provides a contact device for establishing a temperature gradient between epithelial tissue and underlying dermal tissue. The contact device can include a cooling medium contained therein for cooling the non-targeted epithelial tissue, and/or a radiant energy source coupled thereto for heating tissue at the targeted treatment site. In an exemplary embodiment, the contact device includes a tissue-contacting element, e.g., a cooling plate, that is adapted to be positioned on a skin surface, and that is coupled to a cooling element for cooling the plate to thereby cool the skin surface. Where the contact device contains a radiant energy source, at least a portion of the cooling plate is preferably formed from a heat-conducting material that is transparent to radiant energy for allowing radiant energy from the radiant energy source to pass therethrough. In use, the cooling plate can be positioned directly on the skin surface or a layer of gel or liquid can be disposed between the device and the tissue surface to improve thermal contact with the tissue. The gel or liquid layer can optionally contain a pre-photosensitizing agent. After a desired temperature gradient is established, the contact device can be removed from the epithelial tissue before the targeted treatment site is irradiated with light. The device can optionally include a variety of other components to facilitate use, such as one or more temperature controllers to control the radiant energy source and/or the cooling plate. In another embodiment, the contact device can be coupled to a light source to allow the tissue to be simultaneously cooled and/or heated concurrently while the targeted treatment site is irradiated with light.

In yet another embodiment, metabolism of the pre-photosensitizing agent in non-targeted epithelial tissue surrounding the targeted treatment site can be prevented by chemical inhibition, and in particular by applying a chemical inhibitor to epithelial tissue surrounding the targeted treatment site. The chemical inhibitor can be applied to the epithelial tissue concurrently with, before, or after application of the pre-photosensitizing agent, and the chemical inhibitor can be applied topically, e.g., in a cream, by local injection, or systemically. While a variety of chemical inhibitors can be used, suitable chemical inhibitors include any chemical that is effective to inhibit the conversion of a pre-photosensitizing agent, such as a porphyrin precursor, into a photosensitizing agent, such as a porphyrin. Exemplary chemical inhibitors include, for example, 4,6-dioxoheptanoic acid, succinyl acetone, pridoxal-5-phosphate, zinc ions, ferrous ions, and lead ions.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1A:
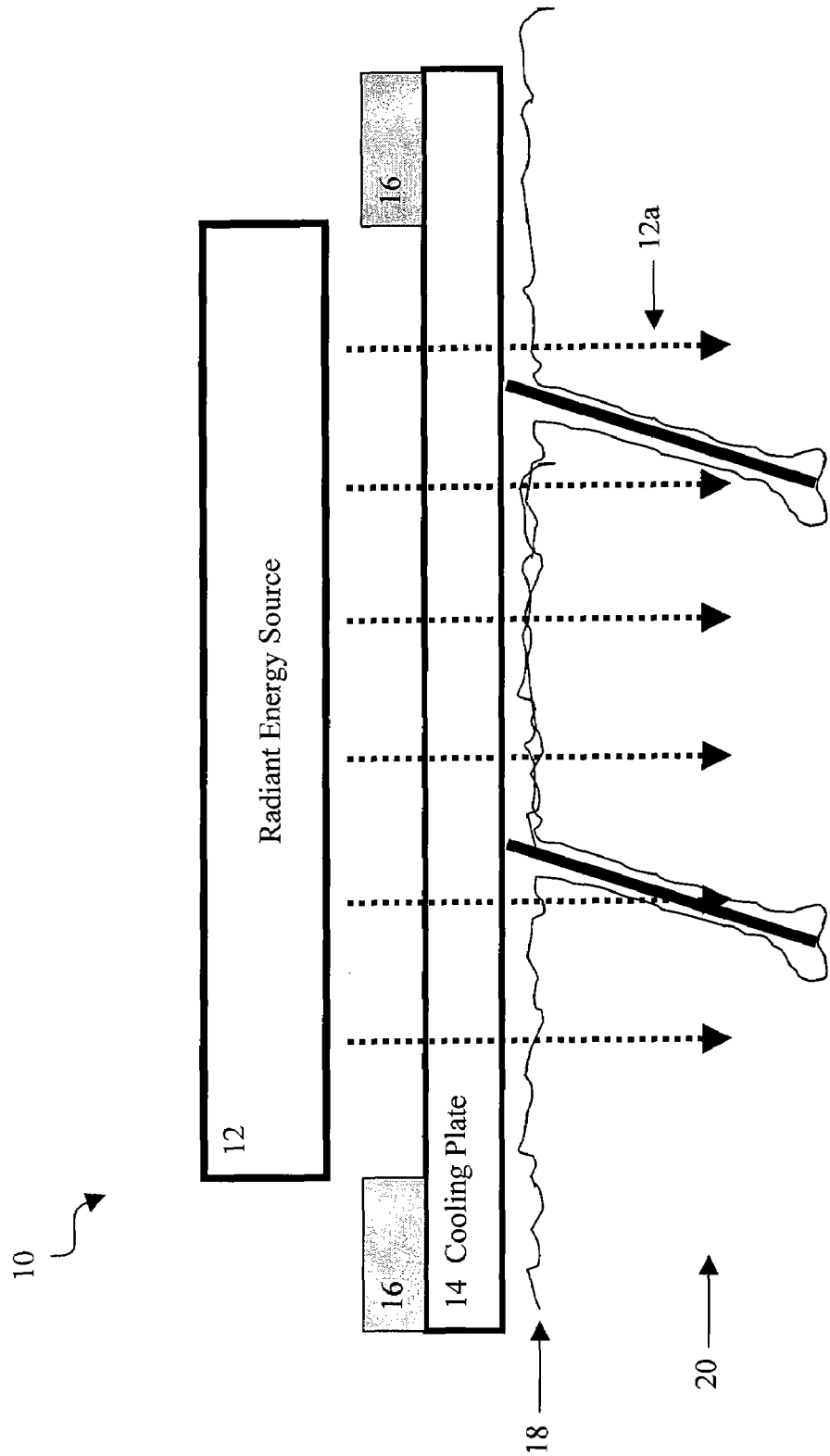
FIG. 1A is a diagram illustrating of one embodiment of a contact device for cooling epithelial tissue and heating dermal tissue at a targeted treatment site in accordance with the present invention.

The methods and devices of the present invention utilize spatial confinement to control formation of a photosensitizing agent from a topically-applied pre-photosensitizing agent. During PDT, a pre-photosensitizing agent, such as the porphyrin precursor ALA, is topically applied to the skin surface, e.g., the epidermal tissue, above a targeted treatment site. This allows the pre-photosensitizing agent to be absorbed through the tissue and into tissue at the targeted treatment site, where the agent metabolizes into a photosensitizing agent, such as the protoporphyrin IX (PpIX). Upon the application of light having an appropriate wavelength, the photosensitizing agent absorbs the light and becomes phototoxic, releasing oxygen to destroy the cells. While ALA-induced PDT has proven effective, accumulation of the pre-photosensitizing agent is not selective and thus the pre-photosensitizing agent can metabolize into a photosensitizing agent in both epithelial tissue and underlying targeted tissue, thereby potentially causing damage to non-targeted, healthy epithelial tissue. The present invention therefore provides methods for preventing or reducing the likelihood of damage to epithelial tissue during PDT.

In general, non-targeted epithelial tissue surrounding a treatment site can be protected by administering a pre-photosensitizing agent to a targeted treatment site, and preventing the metabolic conversion of the pre-photosensitizing agent in the non-targeted epithelial tissue surrounding the treatment site while allowing the pre-photosensitizing agent to metabolize in tissue at the targeted treatment site. The targeted treatment site can then be irradiated with light to activate the photosensitizing agent in the targeted tissue while the epithelial tissue remains substantially unaffected by the light treatment.

The methods and devices of the present invention can be used with a variety of pre-photosensitizing agents, such as porphyrin precursors, but in an exemplary embodiment, the methods of the present invention are used with ALA-induced PDT, which is described in more detail in U.S. Patent Publication No. 2002/0099094A1 entitled "Topical Aminolevulinic Acid-Photodynamic Therapy For The Treatment Of Acne Vulgaris." As disclosed therein, ALA can be used in a variety of forms, including in a pharmacologically equivalent form, such as an amide or ester, or as a salt, such as hydrochloride salt, and it can be topically applied to the skin surface surrounding a targeted treatment site, which underlies the epithelial tissue at the skin surface. A light source, preferably red visible light having a wavelength in the range of about 320 nm to 700 nm, and more preferably about 25 nm to 200 nm, is applied to the targeted treatment site at a dosage of energy in the range of about 1 J/cm$^2$ to 200 J/cm$^2$, and more preferably about 25 J/cm$^2$ to 200 J/cm$^2$. Other suitable photosensitizing agents or pre-photosensitizing agents include, for example, enzyme-activated pre-photosensitizer constructs, such as protease-sensitive oligopeptide conjugates, caged photosensitizers which are un-caged by an enzyme action, temperature dependent liposomal photosensitizers, porphyrins, chlorines, porphycenes, purpurins, phthalocyanines, naphthalocyanines, bacteriochlorins, benzophenothiazines, either as free agents or in combination with specific delivery agents such as in liposomes or as photosensitizer conjugates with targeting molecules, such as peptides, receptor ligands or antibodies.

While various techniques can be used to prevent metabolism of the pre-photosensitizing agent in epithelial tissue surrounding the treatment site, in one embodiment the method utilizes thermal inhibition. In particular, a temperature gradient can be created between the non-targeted epithelial tissue and tissue at the targeted treatment site such that the epithelial tissue has a temperature that is less than the temperature of the underlying targeted tissue. The temperature gradient can be achieved by cooling the non-targeted epithelial tissue under spatially-controlled conditions, and/or by heating the underlying tissue at the targeted treatment site. While heating alone can be effective to establish the desired temperature gradient, the skin is preferably cooled since lower surface temperatures inhibit the pre-photosensitizing agent from metabolizing into a photosensitizing agent in the epithelial tissue. Epithelial cooling with simultaneous targeted warming can be even more advantageous because it creates a steady state that allows the pre-photosensitizing agent to metabolize in the targeted treatment site, e.g., dermal epithelial structures (skin appendages, or localized tumors), while the metabolism rate in the epithelial tissue (non-targeted normal tissue) is greatly reduced if not abolished. In use, when the tissue is irradiated with light, the targeted tissue will be destroyed while damage to the epithelial tissue is substantially prevented. It is possible, however, that the non-targeted epithelial tissue will contain small amounts of the photosensitizing agent, however these amounts should be insubstantial and should not result in any significant damage to the epithelial tissue.

While virtually any surface cooling technique can be used to create a temperature gradient between epithelial tissue and the underlying targeted tissue, in an exemplary embodiment the epithelial tissue, e.g., the epidermis, is cooled using a contact device containing a cooling medium, such as a solid, liquid, or gas medium. The contact device can also be adapted to heat the underlying dermal tissue, and the heat can optionally be applied during simultaneous cooling of the epithelial tissue. In other embodiments, an active cooling source can be used, such as a pump or cryogen spray, or a passive cooling source can be used, such as water evaporation.

Figure 1B:
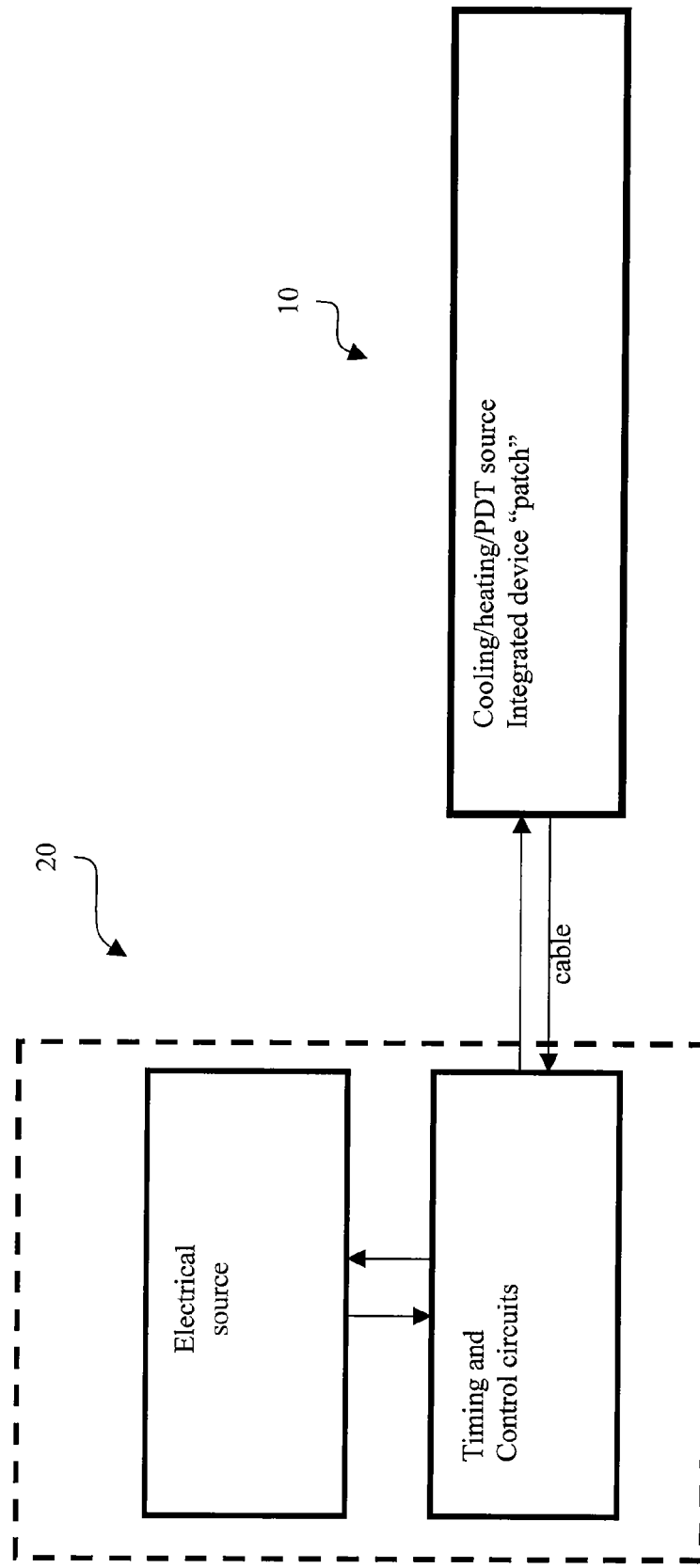
FIG. 1B is a chart illustrating the components of the contact device shown in FIG. 1A.

FIGS. 1A-1B illustrate an exemplary embodiment of a contact device 10 in accordance with the present invention. As shown, the device 10 generally includes a cooling plate 14 that is adapted to be positioned on a skin surface, e.g., on epidermal tissue 18, a cooling element 16 that is effective to cool the cooling plate 14, a radiant energy source 12 that is coupled to the cooling plate 14, and an electrical source and timing and control circuits 20. While not illustrated, the device 10 can be powered by a small portable electrical source such as a battery pack. The entire PDT treatment including use of this invention could be ambulatory in this way.

The cooling plate 14 can have a variety of shapes, sizes, and configurations depending on the intended use, and the plate 14 can be formed from a flexible or rigid material. In an exemplary embodiment, the plate 14 has a diameter that is in the range of about 5 mm to 20 cm. In order to cool the plate 14, a cooling medium can be contained within the plate or a cooling element 16 can be coupled to the plate 14, as shown in FIG. 1A. The cooling element can consist of, for example, a circulated cool liquid, ice, a heat exchanger, cryogen, or a pump, such as a thermoelectric Peltier device.

As previously stated, the contact device 10 can also optionally be adapted to heat the underlying targeted tissue, preferably while simultaneously cooling non-targeted tissue, e.g., the epidermis, as is further shown in FIGS. 1A-1B. While various techniques can be used to heat the dermal tissue, a radiant energy source 12 is preferably utilized that can be directed through the plate 14 to heat only the underlying dermal tissue 20. The plate 14, or at least a portion of the plate 14, is therefore preferably formed from a material that is transparent to radiant energy, such as a heat-conducting material. The radiant energy source 12 can vary, and by way of non-limiting example, suitable radiant energy sources include visible light, infrared light, microwave energy, ultrasound, and radiofrequency energy. Preferred wavelengths are in the range of about 700 nm to 2000 nm. The radiant energy source is also preferably effective to transmit radiant energy at an irradiance in the range of about 50 mW/cm$^2$ to 500 mW/cm$^2$, depending on the source and temperature of the cooling plate 14. In a preferred embodiment, the radiant energy source is an array of light-emitting diodes (LEDs) that are capable of triggering the photosensitizing agent. For example, where ALA is the pre-photosensitizing agent, the LEDs can be 625-650 nm LEDs.

In use, the contact device is placed on the tissue surface, e.g., on the epidermal tissue surface, immediately after or during topical application of a pre-photosensitizing agent, and cooling and/or heating is continued until a desired temperature gradient is established between the non-targeted tissue and the underlying targeted tissue. Depending on the type of cooling medium and/or radiant energy source, epidermal cooling and/or dermal heating can be applied continuously or intermittently, but regardless the external radiant energy source and the external cooling source are preferably adjusted to provide control over both the epidermal and the dermal temperatures. One advantage of this method is that dermal temperatures can be controlled to be less than, equal to, or greater than the core body temperature of the patient. Simultaneous cooling and heating is particularly advantageous in that a steady-state temperature gradient can be achieved such that conversion of the pre-photosensitizing agent to a photosensitizer is inhibited in the epidermis and it is not inhibited or promoted in the underlying target tissue.

While the temperature gradient may vary depending on the intended use, in one embodiment the epithelial tissue can be cooled and/or the targeted treatment site in the underlying tissue can be heated until a temperature gradient in the range of at least about 5° C. is established therebetween. More particularly, the non-targeted epithelial tissue can be cooled to a temperature that is equal to or less than about 25° C., and more preferably that is in the range of about 20° C. to about −5° C., and/or the targeted treatment site in the underlying tissue can be heated to a temperature that is equal to or greater than about 25° C., and more preferably that is in the range of about 25° C. to about 40° C. In an exemplary embodiment, the epithelial tissue is maintained at temperatures about 10° C. and the underlying targeted tissue is maintained at temperatures around 36° C. Once the desired temperature gradient is established, the contact device containing the cooling medium and/or the radiant energy source can be removed from the treatment site to allow the treatment site to be irradiated to activate the photosensitizing agent, thereby causing membrane damage and cell destruction within tissue at the targeted treatment site while the non-targeted epithelial tissue remains substantially unaffected.

In an alternative embodiment, the cooling medium and/or the radiant energy source can be applied to the tissue simultaneous with the application of radiation. This can be achieved by utilizing a contact device that contains an irradiating light source. Thus, the contact device allows the epithelial tissue to be cooled by the cooling medium, and/or the targeted treatment site in the underlying tissue to be heated by the radiant energy source, while light is applied to the targeted treatment site. A person skilled in the art will appreciate that a variety of other techniques can be used to simultaneously irradiate and heat and/or cool the skin.

The methods of the present invention can be used for various applications. In one embodiment, by way of non-limiting example, the epidermis can be protected during PDT for removing hair. In use, a pre-photosensitizing agent can be topically applied to the epidermal tissue surface above the targeted treatment site, and a temperature gradient can be established between the epidermis and the targeted treatment site in the dermis. The cooling of the epidermal skin surface inhibits metabolism of the pre-photosensitizing agent therein, and thus allows the pre-photosensitizing agent to metabolize into a photosensitizing agent in the hair follicles. Irradiating light can then be applied to the targeted treatment site to destroy the hair follicles without damaging the epidermis. As indicated above, the treatment light exposure can be done with or without concurrent surface cooling and/or radiant warming.

In another application, the method can be used to treat acne. Again, a pre-photosensitizing agent is applied to the treatment site and a temperature gradient is established between the epidermis and the targeted treatment site. Since acne occurs below the surface, the cooling of the skin surface will prevent the pre-photosensitizing agent from metabolizing in the epidermis, while allowing the pre-photosensitizing agent to metabolize into a photosensitizing agent at the treatment site. The application of light to the skin will thereby destroy the acne.

In yet another embodiment, the method can be used to treat skin cancer. In this embodiment, a pre-photosensitizing agent is applied to the skin and a temperature gradient can be established between the epidermis and the targeted treatment site to protect non-cancerous skin cells in the epidermis. The temperature gradient allows the pre-photosensitizing agent to metabolize into a photosensitizing agent at the tumor site, thereby allowing the PDT to destroy the tumor cells while preventing damage to healthy epidermal tissue.

In another method according to the present invention, metabolism of a pre-photosensitizing agent in epithelial tissue surrounding a targeted treatment site can be prevented through chemical inhibition. In particular, a chemical inhibitor, such as an enzyme inhibitor, can be applied to the epithelial tissue surrounding the targeted treatment site to prevent a pre-photosensitizing agent from metabolizing into a photosensitizing agent, e.g., a photoactive species, in epithelial tissue. Where ALA is used, for example, the chemical inhibitor is effective to prevent the conversion version of ALA to the photoactive protoporphyrin IX (PpIX) in healthy, non-targeted tissue. As a result, when irradiating light is applied to treat the targeted tissue, the non-targeted epithelial tissue remains substantially unaffected.

A variety of chemical inhibitors can be used with the method of the present invention, but the chemical inhibitor should be effective to inhibit metabolism of a pre-photosensitizing agent, such as a porphyrin precursor, into a photosensitizing agent, such as a porphyrin. In an exemplary embodiment, the chemical inhibitor is 4,6-dioxoheptanoic acid, succinyl acetone, pridoxal-5-phosphate, and inhibitors containing zinc, ferrous ions, or lead ions, as well as combinations and derivatives thereof. The chemical inhibitor can be applied topically, by local injection, or systemically, and it can be applied before or after application of the pre-photosensitizing agent, or simultaneously with the pre-photosensitizing agent. The chemical inhibitor, and optionally the pre-photosensitizing agent, can also be contained within a cream that is topically applied to the skin surface. Suitable creams include, for example, emollients, acid-mantel cream, lotions, oil and water emulsions, and other vehicles known in the art.

The concentration of the chemical inhibitor can also vary, but in an exemplary embodiment the chemical inhibitor is applied at a concentration that is equal to or greater than about 0.1%, and is preferably applied to the skin surface for a duration of at least about 15 minutes. The skin surface can subsequently be washed to allow a photosensitizing agent to be applied thereto.

Chemical inhibition can be used for a variety of applications, and in one embodiment it can be used to suppress unwanted epidermal damage and still allow the removal of unwanted hair. In particular, an inhibitor is applied to the epidermis to decrease metabolism of a pre-photosensitizing applied to the epidermis, while allowing deeper formation of the photosensitizing agent to occur in the hair follicles. This enables the desired efficient removal of unwanted hair while minimizing epidermal damage. Similarly, chemical inhibition can be used to treat acne by allowing PDT to be targeted to the deeper-seated sebaceous glands, while minimizing or preventing damage to the epidermis. Chemical inhibition can also be used, for example, to protect normal tissue surrounding malignant cells.

The followings examples serve to further illustrate the present invention.

EXAMPLE 1

Figure 2:
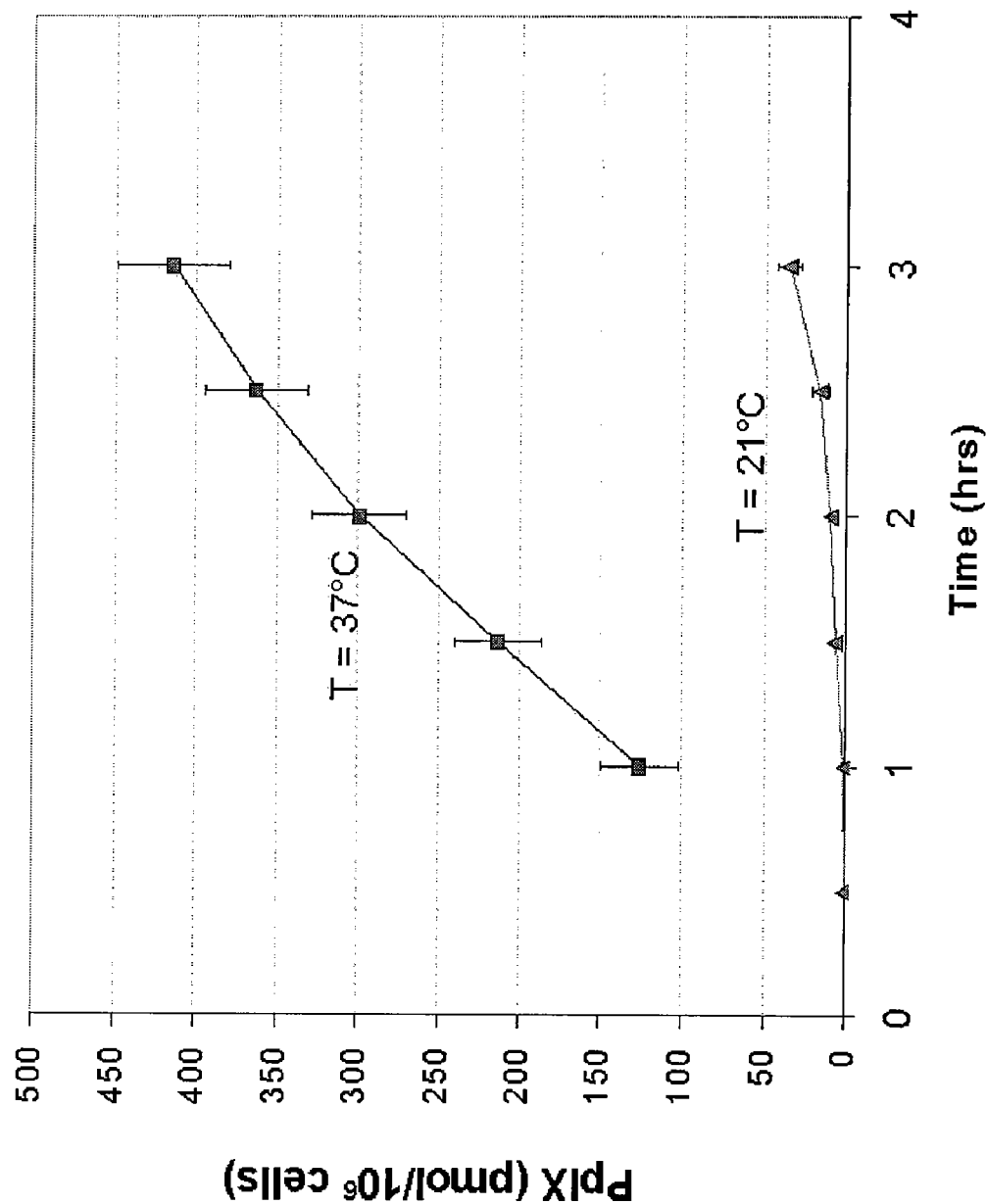
FIG. 2 is a chart illustrating the effect of temperature on the formation of PpIX in rat epidermal keratinocyte cells incubated with 0.5 mM ALA.

Two trials of rat epidermal keratinocyte (REK) cells were incubated with 0.5 mM ALA at temperatures of 21° C. and 37° C., respectively, for varying times. As shown in FIG. 2, incubation at 21° C. resulted in a significant decrease in PpIX formation as compared to incubation at 37° C. For example, after three hours, the cells at 37° C. had a PpIX concentration greater than 400 pmol/$10^6$, while the cells at 37° C. had a PpIX concentration less than 50 pmol/$10^6$. Accordingly, a temperature gradient of about 16° C. is more than sufficient to inhibit metabolism of a photosensitizing agent in epidermal tissue surrounding a targeted treatment site.

EXAMPLE 2

Figure 3:
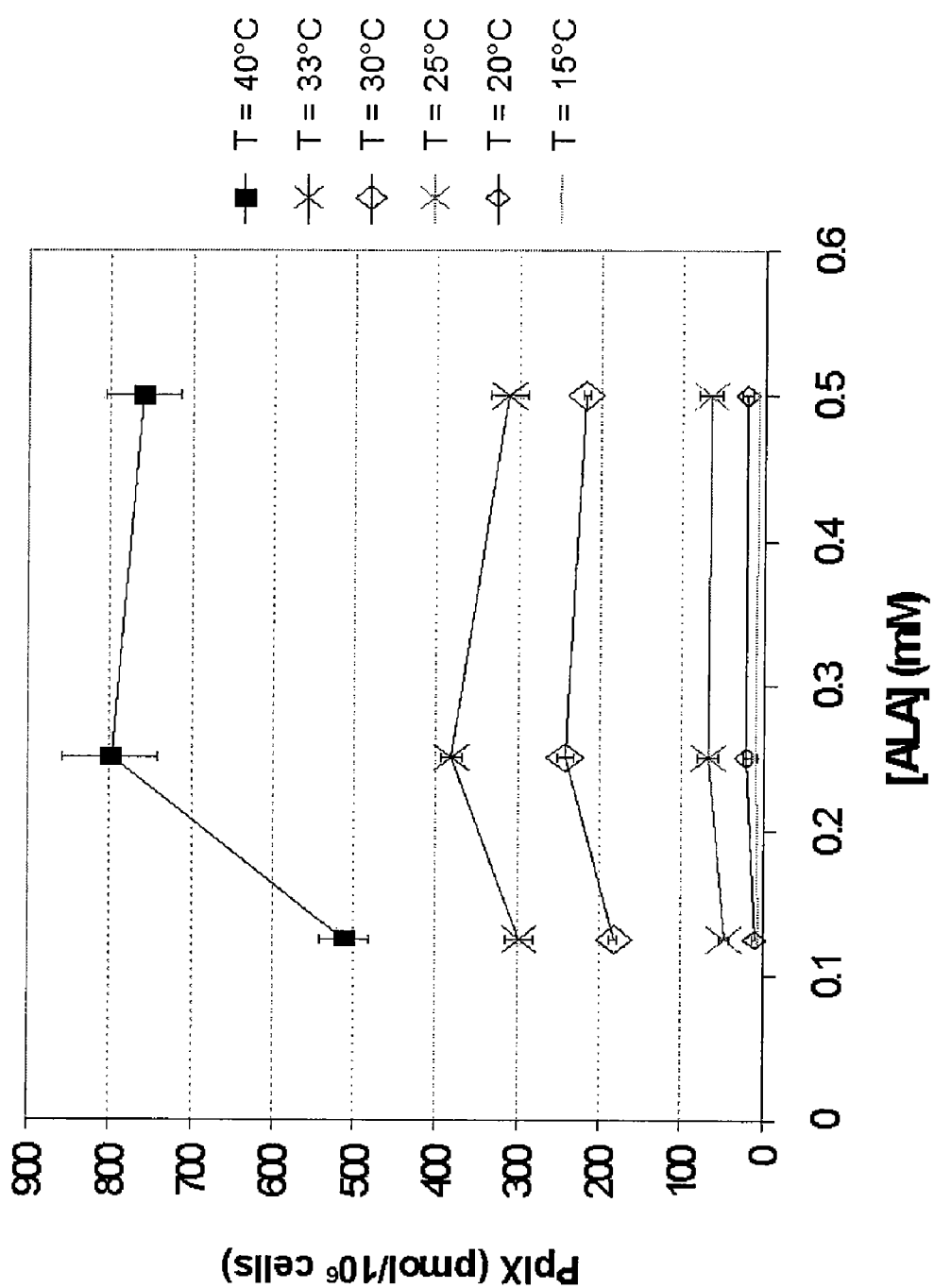
FIG. 3 is another chart illustrating the effect of temperature on the formation of PpIX in rat epidermal keratinocyte cells incubated with various concentrations of ALA.

Several trials of rat epidermal keratinocyte (REK) cells were incubated with various amounts of ALA ranging from 0.1 mM to 0.5 mM, at various temperatures ranging from 15° C. to 40° C. As shown in FIG. 3, PpIX formation was significantly inhibited in cells having a temperature of about 25° C. or less. PpIX formation increased significantly in cells having a temperature of about 30° C. or more.

EXAMPLE 3

Figure 4:
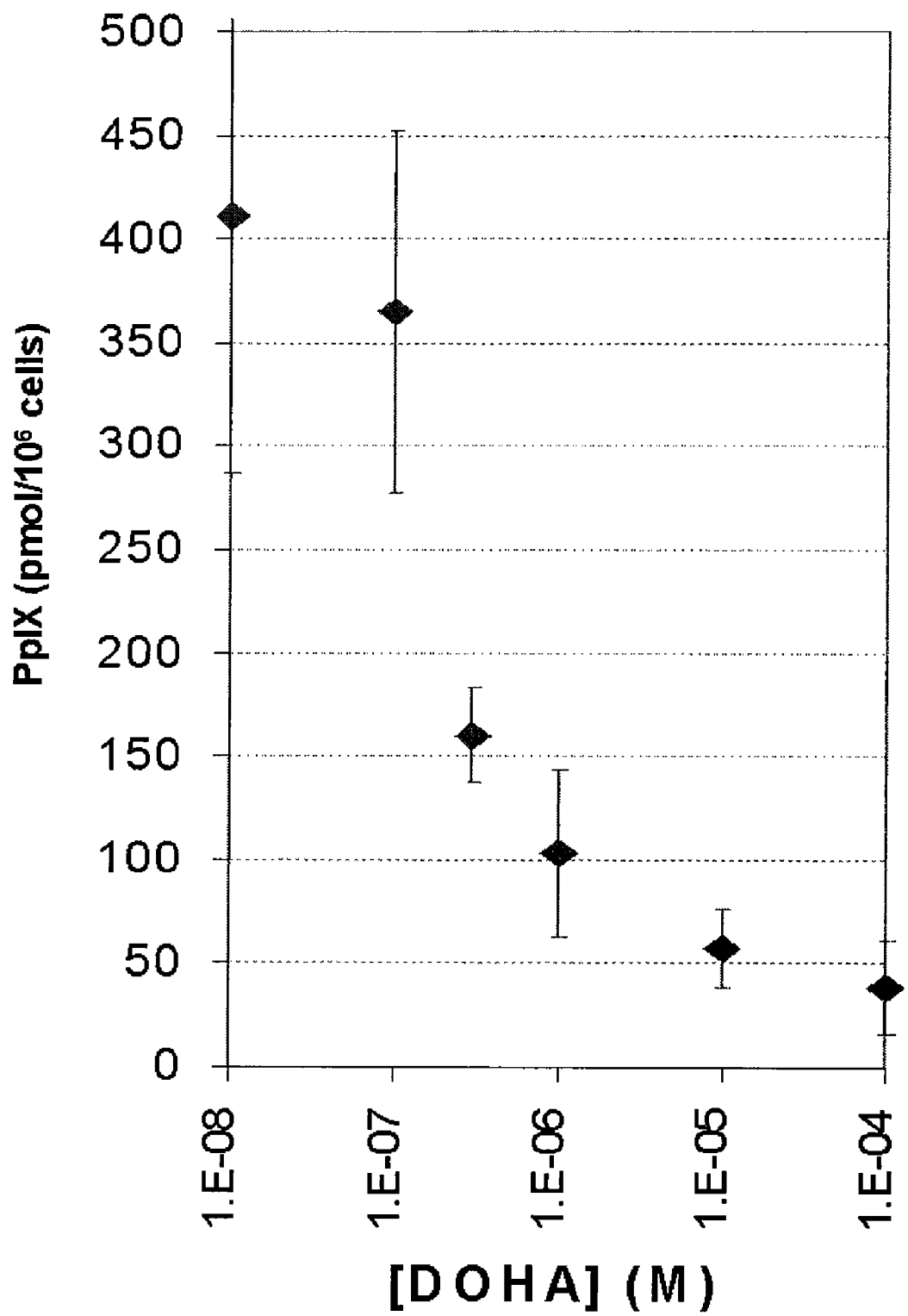
FIG. 4 is a chart illustrating the effect of 4,6-dioxoheptanoic on the formation of PpIX in rat epidermal keratinocyte cells incubated with 0.25 mM ALA.

Several trials of rat epidermal keratinocyte (REK) cells were pre-incubated with various amounts of 4,6-dioxoheptanoic acid (DOHA) ranging from $1^{-8}$ M to $1^{-4}$ M. The cells were then washed, and incubated with 0.25 mM ALA for 3 hours. As shown in FIG. 4, PpIX formation in cells chemically treated with DOHA at concentrations greater than $10^{-7}$ M was significantly inhibited, and even further chemical inhibition occurred at DOHA concentrations greater than $10^{-5}$ M.

EXAMPLE 4

Figure 5B:
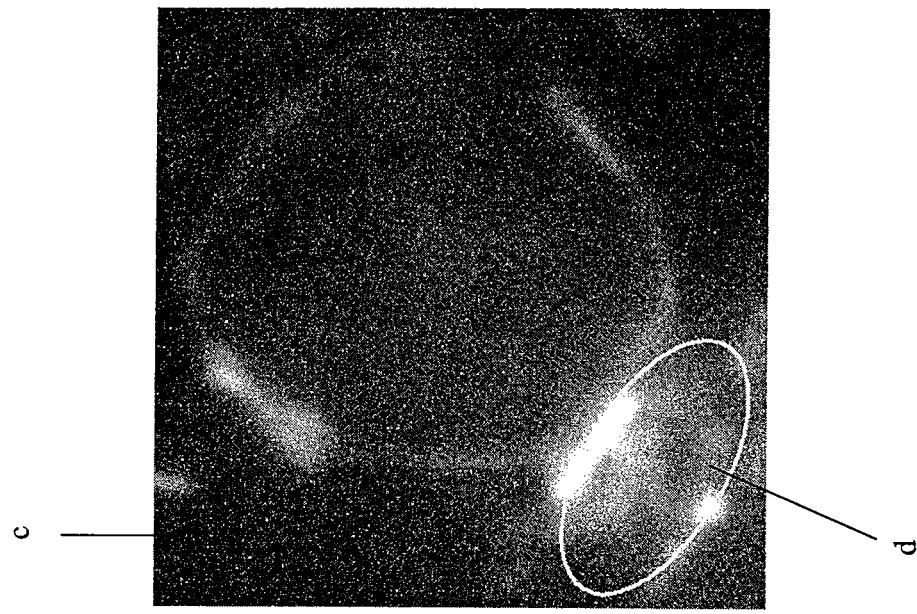
FIG. 5B is another fluorescence micrograph showing the effect of temperature on the formation of PpIX in human skin treated with a 2% solution of ALA.
Figure 5A:
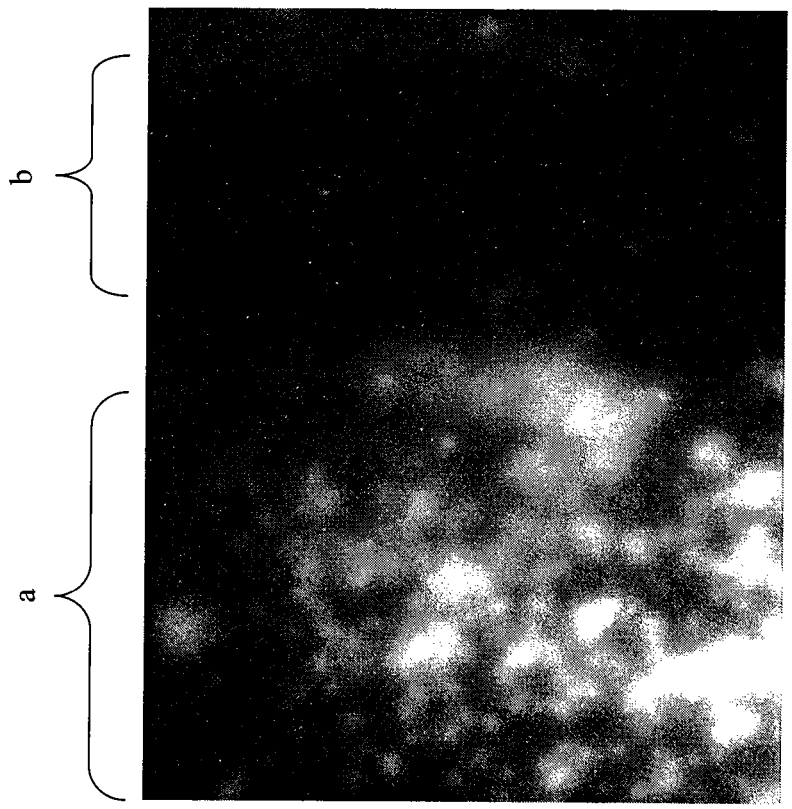
FIG. 5A is a fluorescence micrograph showing the effect of temperature on the formation of PpIX in human skin treated with a 2% solution of ALA.

A 2% ALA solution was iontophoretically transferred into human skin. As shown in FIGS. 5A-5B, PpIX fluorescence (shown by white areas) was imaged after a 3-hour incubation (a) at room temperature, and at 10-15° C. (measured at the skin surface), achieved by (b) contact cooling and (c) convection cooling. As shown in FIG. 5A, ALA-induced PpIX formation was thermally inhibited in vivo in human skin (b) that was cooled by contact to 10-15° C., whereas significant PpIX formation is shown in the area of skin that was treated at room temperature. As shown in FIG. 5B, baseline ALA-induced PpIX fluorescence, as circled and indicated by reference d, is seen in an area that is immediately outside the cooling apparatus.

EXAMPLE 5

Figure 6:
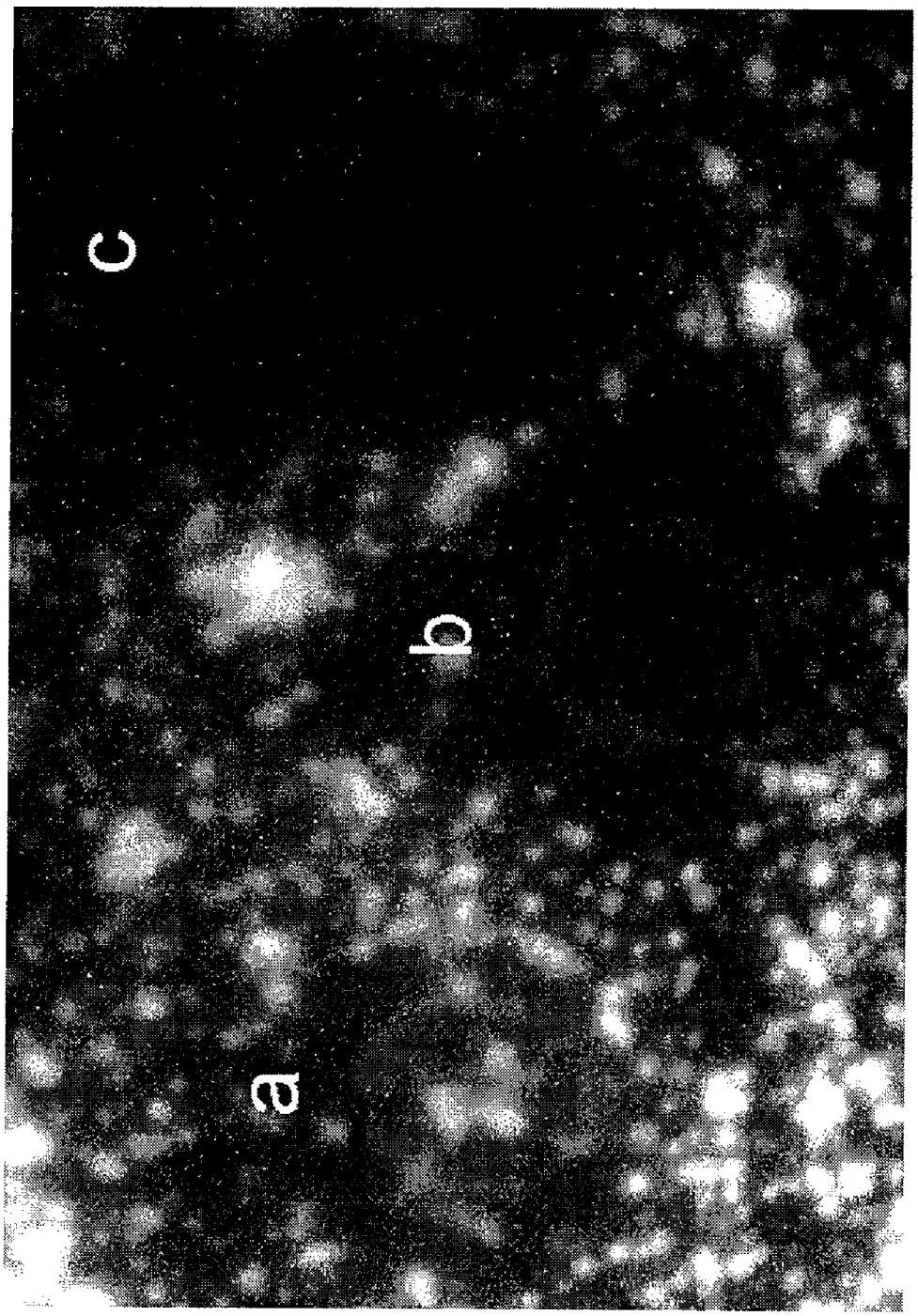
FIG. 6 is a fluorescence micrograph showing the effect of 4,6-dioxoheptanoic on the formation of PpIX in human skin treated with a varying concentrations of ALA.

DOHA was topically applied to human skin in concentrations of (a) 0.1%, (b) 0.3%, and (c) 1% for 1 hour, followed by topical application of 5% ALA. PpIX fluorescence was then imaged. As shown in FIG. 6, increasing concentrations of DOHA were effective to chemically inhibit PpIX formation in human skin in vivo.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for protecting epithelial tissue during photodynamic therapy using a pre-photosensitizing agent, the method comprising the steps of:
    administering a pre-photosensitizing agent to epithelial tissue and a targeted treatment site underlying the epithelial tissue;
    preventing metabolism of the pre-photosensitizing agent in the epithelial tissue, while allowing the pre-photosensitizing agent to metabolize into a photosensitizing agent in tissue at the targeted treatment site; and
    irradiating the targeted treatment site to activate the photosensitizing agent at the targeted treatment site, wherein the epithelial tissue is substantially unaffected,
    wherein the step of preventing metabolism of the pre-photosensitizing agent in epithelial tissue comprises creating a temperature gradient between the epithelial tissue and tissue at the targeted treatment site.

2. The method of claim 1, wherein the temperature gradient is created before the step of irradiating.

3. The method of claim 1, wherein the temperature gradient is created by cooling the epithelial tissue.

4. The method of claim 3, wherein the step of cooling comprises the step of positioning a contact device containing a cooling medium on the epithelial tissue.

5. The method of claim 4, wherein the cooling medium is selected from the group consisting of a solid, liquid, and a gas medium.

6. The method of claim 4, wherein the contact device further includes a radiant energy source that is effective to heat tissue at the targeted treatment site.

7. The method of claim 6, wherein at least a portion of the contact device is transparent for allowing radiant energy from the radiant energy source to pass therethrough.

8. The method of claim 4, wherein the contact device is removed from the epithelial tissue before the targeted treatment site is irradiated with light.

9. The method of claim 4, wherein the contact device is coupled to a light source for irradiating the targeted treatment site.

10. The method of claim 3, wherein the epithelial tissue is cooled concurrently while the targeted treatment site is irradiated with light.

11. The method of claim 3, wherein the epithelial tissue is cooled to a temperature that differs from a temperature of tissue at the targeted treatment site by at least about 5° C.

12. The method of claim 3, wherein the epithelial tissue is cooled to a temperature that is equal to or less than about 25° C.

13. The method of claim 3, wherein the epithelial tissue is cooled to a temperature in the range of about 20° C. to −5° C.

14. The method of claim 1, wherein the temperature gradient is created by cooling the epithelial tissue and heating tissue at the targeted treatment site.

15. The method of claim 14, wherein the tissue at the targeted treatment site is heated to a temperature that is equal to about 25° C.

16. The method of claim 14, wherein the tissue at the targeted treatment site is heated to a temperature in the range of about 25° C. to 40° C.

17. The method of claim 14, wherein the step of heating the tissue at the targeted treatment site comprises delivering a radiant energy source to the tissue.

18. The method of claim 17, wherein the radiant energy source is selected from the group consisting of visible light, infrared light, microwave energy, ultrasound, and radiofrequency energy.

19. A method for protecting epithelial tissue during photodynamic therapy using a pre-photosensitizing agent, the method comprising the steps of:
   administering a pre-photosensitizing agent to epithelial tissue and a targeted treatment site underlying the epithelial tissue;
   preventing metabolism of the pre-photosensitizing agent in the epithelial tissue, while allowing the pre-photosensitizing agent to metabolize into a photosensitizing agent in tissue at the targeted treatment site; and
   irradiating the targeted treatment site to activate the photosensitizing agent at the targeted treatment site, wherein the epithelial tissue is substantially unaffected,
   wherein the targeted treatment site comprises malignant cells, and the step of irradiating the targeted treatment site is effective to substantially destroy the malignant cells.

20. A method for protecting epithelial tissue during photodynamic therapy using a pre-photosensitizing agent, the method comprising the steps of:
   administering a pre-photosensitizing agent to epithelial tissue and a targeted treatment site underlying the epithelial tissue;
   preventing metabolism of the pre-photosensitizing agent in the epithelial tissue, while allowing the pre-photosensitizing agent to metabolize into a photosensitizing agent in tissue at the targeted treatment site; and
   irradiating the targeted treatment site to activate the photosensitizing agent at the targeted treatment site, wherein the epithelial tissue is substantially unaffected,
   wherein the targeted treatment site comprises a patient's sebaceous glands, and the step of irradiating the targeted treatment site is effective to treat acne.

21. A method for protecting epithelial tissue during photodynamic therapy induced using a pre-photosensitizing agent, the method comprising the steps of:
   administering a pre-photosensitizing agent to epithelial tissue and a targeted treatment site underlying the epithelial tissue;
   preventing metabolism of the pre-photosensitizing agent in the epithelial tissue, while allowing the pre-photosensitizing agent to metabolize into a photosensitizing agent in tissue at the targeted treatment site; and
   irradiating the targeted treatment site to activate the photosensitizing agent at the targeted treatment site, wherein the epithelial tissue is substantially unaffected,
   wherein the targeted treatment site comprises a patient's hair follicles, and the step of irradiating the targeted treatment site is effective to substantially remove hair associated with the hair follicles.

22. The method of claim 14, wherein the tissue at the targeted treatment site is heated to a temperature that is greater than 25° C.

23. The method of claim 1, wherein the step of irradiating the targeted treatment site comprises maintaining at least a portion of the targeted treatment site at a temperature in a range between about 25° C. and about 40° C.

24. A method for protecting epithelial tissue during photodynamic therapy using a pre-photosensitizing agent, the method comprising the steps of:
   administering a pre-photosensitizing agent to epithelial tissue and a targeted tissue underlying the epithelial tissue;
   preventing metabolism of the pre-photosensitizing agent in the epithelial tissue, while allowing the pre-photosensitizing agent to metabolize into a photosensitizing agent in the targeted tissue; and
   irradiating the epithelial tissue and the targeted tissue, with the targeted tissue at a temperature in a range between about 25° C. and about 40° C. during the irradiation, to activate the photosensitizing agent in the targeted tissue without substantially affecting the epithelial tissue.

25. The method of claim 24, wherein the epithelial tissue and the targeted tissue are irradiated with the epithelial tissue at a temperature that is less than the temperature of the targeted tissue.

* * * * *

UNITED STATES PATENT AND TRADEMARK OFFICE
CERTIFICATE OF CORRECTION

| | | |
|---|---|---|
| PATENT NO. | : 7,659,301 B2 | Page 1 of 1 |
| APPLICATION NO. | : 10/709122 | |
| DATED | : February 9, 2010 | |
| INVENTOR(S) | : Anderson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1109 days.

Signed and Sealed this

Thirtieth Day of November, 2010

David J. Kappos
*Director of the United States Patent and Trademark Office*